(12) United States Patent
Markworth et al.

(10) Patent No.: US 9,386,975 B2
(45) Date of Patent: Jul. 12, 2016

(54) INTERBODY DISTRACTOR

(71) Applicant: Custom Spine Acquisition, Inc., Marietta, GA (US)

(72) Inventors: Aaron Markworth, Flanders, NJ (US); Kevin Sichler, West Orange, NJ (US)

(73) Assignee: Amendia, Inc., Marietta, GA (US)

( * ) Notice: Subject to any disclaimer, the term of this patent is extended or adjusted under 35 U.S.C. 154(b) by 742 days.

(21) Appl. No.: 13/875,611

(22) Filed: May 2, 2013

(65) Prior Publication Data
US 2014/0330280 A1    Nov. 6, 2014

(51) Int. Cl.
*A61B 17/68*    (2006.01)
*A61B 17/02*    (2006.01)
*A61F 2/46*    (2006.01)
*A61F 2/30*    (2006.01)

(52) U.S. Cl.
CPC ............. *A61B 17/025* (2013.01); *A61F 2/4611* (2013.01); *A61F 2/4684* (2013.01); *A61B 2017/0256* (2013.01); *A61F 2002/30266* (2013.01); *A61F 2002/30471* (2013.01); *A61F 2002/30556* (2013.01); *A61F 2002/4623* (2013.01); *A61F 2002/4627* (2013.01)

(58) Field of Classification Search
CPC ...................... A61B 17/025; A61B 2017/0256; A61F 2/4601; A61F 2/4611; A61F 2/4644; A61F 2/4657; A61F 2002/4661; A61F 2002/4658; A61F 2002/4659; A61F 2/4684
See application file for complete search history.

(56) References Cited

U.S. PATENT DOCUMENTS 6,193,757 B1 *    2/2001    Foley .................... A61F 2/4455
                                                                623/17.16

OTHER PUBLICATIONS

In'tech Medical Manufacturing Solutions; Cage Inserter; 11 pages, accessed Jan. 14, 2013. http://www.intech-medical.com/index.php?option=com_content&task=view&id=54&Itemid=51.

* cited by examiner

*Primary Examiner* — Anu Ramana
(74) *Attorney, Agent, or Firm* — Rahman LLC

(57) ABSTRACT

An interbody distractor and geometry trial instrument to measure a height and an angle for an associated implant includes a height handle and an expansion head coupled to the height handle that is adapted to be positioned in a vertebral body. A wedge sleeve is coupled to the expansion head, to control an angle of a first surface plate and a second surface plate of the expansion head when the wedge sleeve interacts with the expansion head. A wedge sleeve knob is adapted to drive the wedge sleeve linearly towards the vertebral body when the wedge sleeve knob is actuated. A height of the expansion head and an angle of the first and the second surface plate are measured to determine the height and the angle of the associated implant when the height handle and the wedge sleeve knob are actuated.

22 Claims, 16 Drawing Sheets

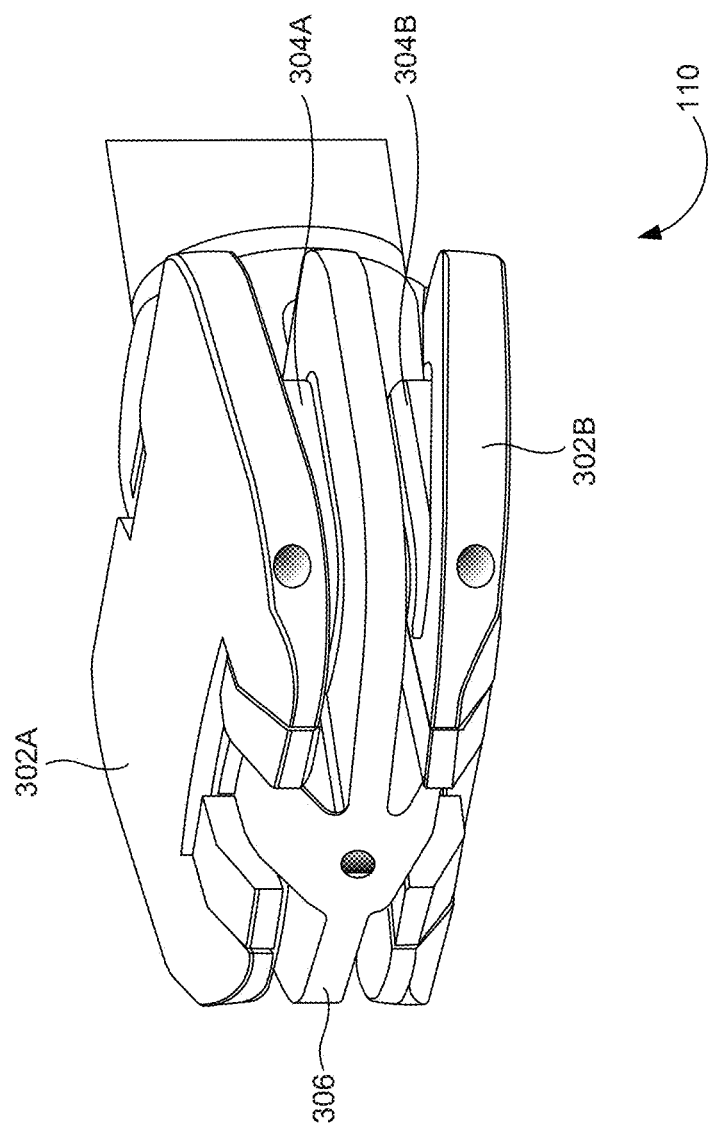

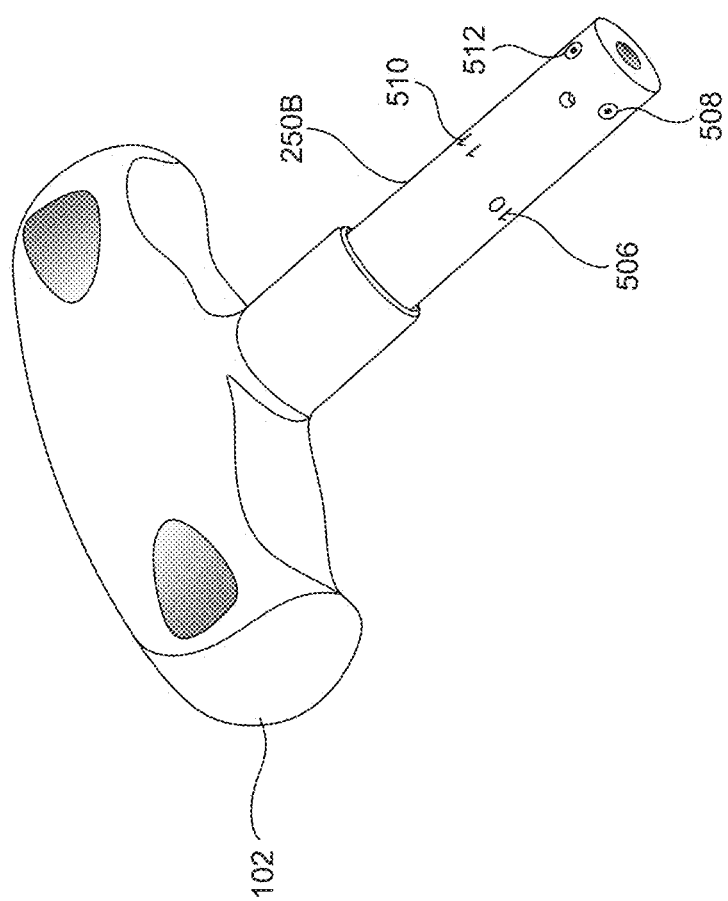

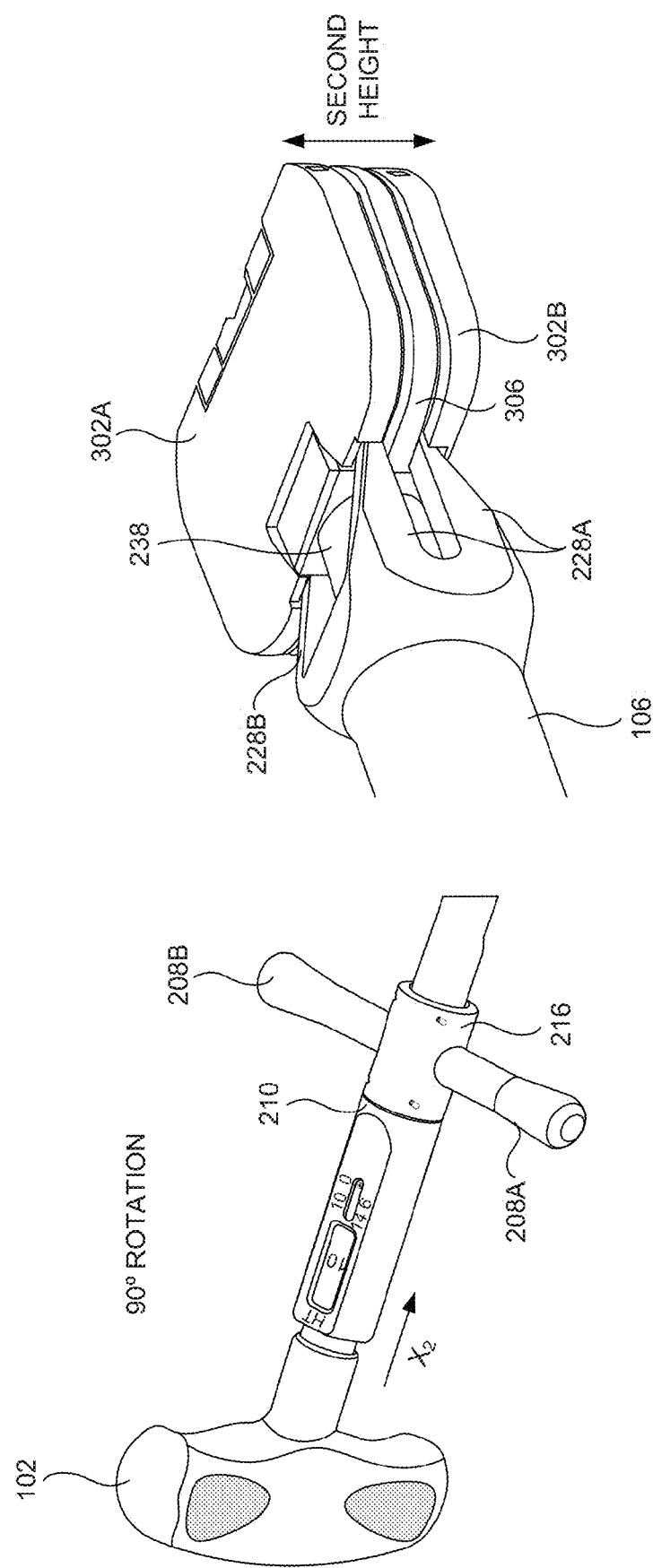

INTERBODY DISTRACTOR

BACKGROUND

1. Technical Field

The embodiments herein generally relate to medical devices, and, more particularly, to inserter devices used during orthopedic surgeries.

2. Description of the Related Art

Intervertebral disc degeneration often leads to chronic lower back pain that occurs with aging. Due to variable spinal anatomy, it is often difficult to seat intervertebral body devices properly to support the best quality bone during surgery. Thus, poor placement and subsidence of implants can occur leading to implant failure and diseases of the spine such as kyphosis (e.g., a curvature of the upper spine which can be either the result of bad posture or a structural anomaly in the spine), and lordosis (e.g., an inward curvature of a portion of the vertebral column). This may also be due to abnormal loading patterns on the disc or inappropriate means of distracting the disc space. Passing various size footprints (e.g., use of multiple instruments such as standard footprints and height trials, multiple trial instruments, distractor and trial inserters, medical cage inserters, etc.) by sensitive vascular and neural anatomy can also cause damage to the structures leading to secondary morbidities.

The standard multiple footprint and height trial instruments require multiple passes by delicate anatomic structures if the correct size is not initially chosen. Further, they are also static in size, and only distract the disc space if an oversize trial is chosen. The combination distractor and trial inserters and cage implant inserters in general are typically large and bulky, and they only allow insertion of standard trial pre-assembled to the same instrument. Distraction maneuvers must be done separately. The wide tips must be inserted into the disc space and stay in a place while the trial is inserted through it. Such combination distractor and trial inserters require multiple assemblies and multiple passes of various trials if the proper size is not initially chosen since they cannot measure angle of deformity at the same time.

Accordingly, there remains a need for a distractor trial assembly that minimizes the number of assemblies and passes of trials for measuring the size and angle of an interbody implant.

SUMMARY

In view of the foregoing, an embodiment herein provides an interbody distractor and geometry trial instrument to measure a height and an angle for an associated implant. The interbody distractor and geometry trial instrument includes a height handle, an expansion head coupled to the height handle. The expansion head includes a first surface plate and a second surface plate. The expansion head is adapted to be positioned in a vertebral body. The interbody distractor and geometry trial instrument includes a wedge sleeve coupled to the expansion head. The wedge sleeve controls an angle of the first surface plate and the second surface plate when the wedge sleeve interacts with the expansion head. A wedge sleeve knob is positioned between the height handle and the wedge sleeve. The wedge sleeve knob is adapted to drive the wedge sleeve linearly towards the vertebral body when the wedge sleeve knob is actuated. A height of the expansion head and an angle of the first surface plate and the second surface plate are measured to determine the height and the angle of the associated implant when the height handle and the wedge sleeve knob are actuated.

The wedge sleeve may include a first pair of arms and a second pair of arms. The first pair of arms includes a first slot. The second pair of arms includes a second slot. The expansion head further includes a first clocking pin, a first lifter adapted to lift the first surface plate, a second lifter adapted to lift the second surface plate, a head frame body positioned between the first slot and the second slot of the first pair of arms and the second pair of arms of the wedge sleeve. The head frame body is adapted to accommodate the first lifter, and the second lifter. The expansion head further includes a first pair of hinge pins adapted to hold the second lifter and the second surface plate such that the first lifter and the first surface plate are held assembled with the head frame body, and a second pair of hinge pins adapted to hold the second lifter and the second surface plate.

The expansion head further includes a pair of assembly screws adapted to capture the second lifter and the second surface plate such that the second lifter and the second surface plate are held assembled with the head frame body. The expansion head distracts a disc space and associated ligamentous tissues in the vertebral body. The interbody distractor further includes a second handle coupled to the wedge sleeve, a middle main shaft that is adapted to fit inside the wedge sleeve, and an inner cam shaft and a cam head that are adapted to fit inside the middle main shaft such that the cam head is assembled coaxial with the inner cam shaft. The cam head adjusts the height of the expansion head and the angle of the first surface plate and the second surface plate when the height handle and the wedge sleeve knob are actuated.

The wedge sleeve knob includes a second clocking pin, a pair of arms adapted to advance the wedge sleeve linearly towards the vertebral body, a gauge sleeve having a first end and a second end. The second end is positioned around the height handle. The gauge sleeve is adapted to translate linearly towards the vertebral body when the pair of arms are actuated. The wedge sleeve knob further includes a wedge sleeve knob housing adapted to accommodate the pair of arms, the first end of the gauge sleeve, and the wedge sleeve, and a pair of cross pins adapted to assemble the gauge sleeve and the wedge sleeve in the wedge sleeve knob housing.

The height handle includes a hole. The interbody distractor further includes a cam shaft fitting adapted to fit in the hole of the height handle. The cam shaft fitting includes a hole and a cross pin hole. The interbody distractor further includes a cross pin adapted to be fitted in the cross pin hole such that the cam shaft fitting holds the inner shaft firmly.

The cam head adjusts the expansion head to a first height when (i) the height handle is at a first angle, and (ii) the wedge sleeve knob translates to a first position. The cam head adjusts the expansion head to a second height when (i) the height handle is at a second angle, and (ii) the wedge sleeve knob translates to a second position. The second position is greater than the first position.

The cam head adjusts the expansion head to a third height when (i) the height handle is at a third angle, and (ii) the wedge sleeve knob translates to a third position. The third position is greater than the second position. The cam head adjusts the expansion head to a fourth height when (i) the height handle is at a fourth angle, and (ii) the wedge sleeve knob translates to a fourth position. The fourth position is greater than the third position. The first angle, the second angle, the third angle, and the fourth angle are separated by a 90 degree interval.

In another aspect, an interbody distractor is provided. The interbody distractor includes a height handle having a hole, an expansion head coupled to the height handle. The expansion head is adapted to be positioned in a vertebral body. The expansion head includes a first clocking pin, a top surface plate and a bottom surface plate positioned opposite to each other, a top lifter adapted to lift the top surface plate, a bottom lifter adapted to lift the bottom surface plate, a head frame body including a top extension and a bottom extension. The head frame body is adapted to accommodate the top lifter, and the bottom lifter. The expansion head further includes a first pair of hinge pins adapted to hold the top lifter and the top surface plate such that the top lifter and the top surface plate are held assembled with the head frame body, a second pair of hinge pins adapted to hold the bottom lifter and the second surface plate, and a pair of assembly screws adapted to capture the bottom lifter and the bottom surface plate such that the bottom lifter and the bottom surface plate are held assembled with the head frame body.

A wedge sleeve is coupled to the expansion head. The wedge sleeve controls an angle of the top surface plate and the bottom surface plate when the wedge sleeve interacts with the top surface plate and the bottom surface plate. The wedge sleeve includes a first pair of arms, and a second pair of arms. The first pair of arms includes a first slot. The second pair of arms includes a second slot. The first slot and the second slot are adapted to accommodate the head frame body. A wedge sleeve knob is positioned between the height handle and the wedge sleeve. The wedge sleeve knob is adapted to drive the wedge sleeve linearly towards the vertebral body when the wedge sleeve knob is actuated. A height of the expansion head and an angle of the top surface plate and the bottom surface plate are measured to determine a height and an angle for an associated implant when the height handle and the wedge sleeve knob are actuated.

The wedge sleeve knob includes a second clocking pin, a pair of arms adapted to advance the wedge sleeve linearly towards the vertebral body, a gauge sleeve having a first end and a second end. The first end is coupled to the wedge sleeve. The second end is positioned around the height handle. The gauge sleeve is adapted to translate linearly towards the vertebral body when the pair of arms are actuated. A wedge sleeve knob housing is adapted to accommodate the pair of arms, the first end of the gauge sleeve, and the wedge sleeve. A pair of cross pins is adapted to assemble the gauge sleeve and the wedge sleeve in the wedge sleeve knob housing.

The interbody distractor further includes a second handle coupled to the wedge sleeve, a middle main shaft adapted to accommodate inside the wedge sleeve, an inner cam shaft adapted to accommodate inside the middle main shaft. The inner cam shaft includes a first end and a second end. The interbody distractor further includes a cam head assembled coaxial with the inner cam shaft. The cam head includes a first end and a second end. The first end of the cam head is adapted to engage the second end of the inner cam shaft. The second end of the cam head is adapted to engage the expansion head such that the inner cam shaft enables the second end of the cam head to drive the top lifter and the bottom lifter to lift the top surface angle plate, and the bottom surface angle plate respectively.

The interbody distractor further includes a cam shaft fitting having a first end and a second end. The first end is adapted to fit in the hole of the height handle. The cam shaft fitting includes a cross pin hole. The second end is adapted to accommodate the second end of the inner cam shaft. The interbody distractor further includes a cross pin adapted to be fitted in the cross pin hole such that the cam shaft fitting holds the second end of the inner shaft firmly.

In yet another aspect, a method of operating an interbody device to measure a height and an angle for an associated implant is provided. The interbody device includes a height handle, a wedge sleeve knob coupled to the height handle, a wedge sleeve coupled to the wedge sleeve knob, and an expansion head coupled to the wedge sleeve. The expansion head includes a top surface angle plate and a bottom surface angle plate. The method includes positioning the expansion head into a vertebral body, actuating the wedge sleeve knob such that the wedge sleeve moves linearly towards the vertebral body, lifting the expansion head, and measuring a height of the expansion head and an angle of the top surface angle plate and the bottom surface angle plate of the expansion head when the height handle and the wedge sleeve knob are actuated.

A calibrated gauge marker may be positioned at each position of the height handle and a corresponding height. The expansion head further includes a head frame body coupled to the top surface angle plate and the bottom surface angle plate, a top lifter positioned between the top surface angle plate and the head frame body, and a bottom lifter positioned between the bottom surface angle plate and the head frame body. The expansion head may be adjusted to a first height when (i) the height handle is at a first angle, and (ii) the wedge sleeve knob translates to a first position. The expansion head may be further adjusted to a second height when (i) the height handle is at a second angle, and (ii) the wedge sleeve knob translates to a second position. The second position is greater than the first position.

The expansion head may be further adjusted to a third height when (i) the height handle is at a third angle, and (ii) the wedge sleeve knob translates to a third position. The third position is greater than the second position. The expansion head may be further adjusted to a fourth height when (i) the height handle is at a fourth angle, and (ii) the wedge sleeve knob translates to a fourth position. The fourth position is greater than the third position. The first angle, the second angle, the third angle, and the fourth angle are separated by a 90 degree interval.

The expansion head may be adjusted to at least one of the first height, the second height, the third height, or the fourth height to enable at least one of (i) a distraction of disc space and associated ligamentous tissues, (ii) a correction of spinal deformity, and (iii) an easier insertion of the associated implant in the vertebral body.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 3A illustrates the expansion head of the interbody distractor trial assembly of FIG. 1 according to an embodiment herein;

FIG. 5B illustrates a perspective view of the height handle coupled to the gauge sleeve having the second marker corresponding to the second reading dot and a third marker corresponding to a third reading dot on the surface of the gauge sleeve according to an embodiment herein;

FIG. 6B illustrates a second height displacement of the expansion head and a second position of the wedge sleeve knob when the height handle is at a second angle according to an embodiment herein;

DETAILED DESCRIPTION

Figure 1:
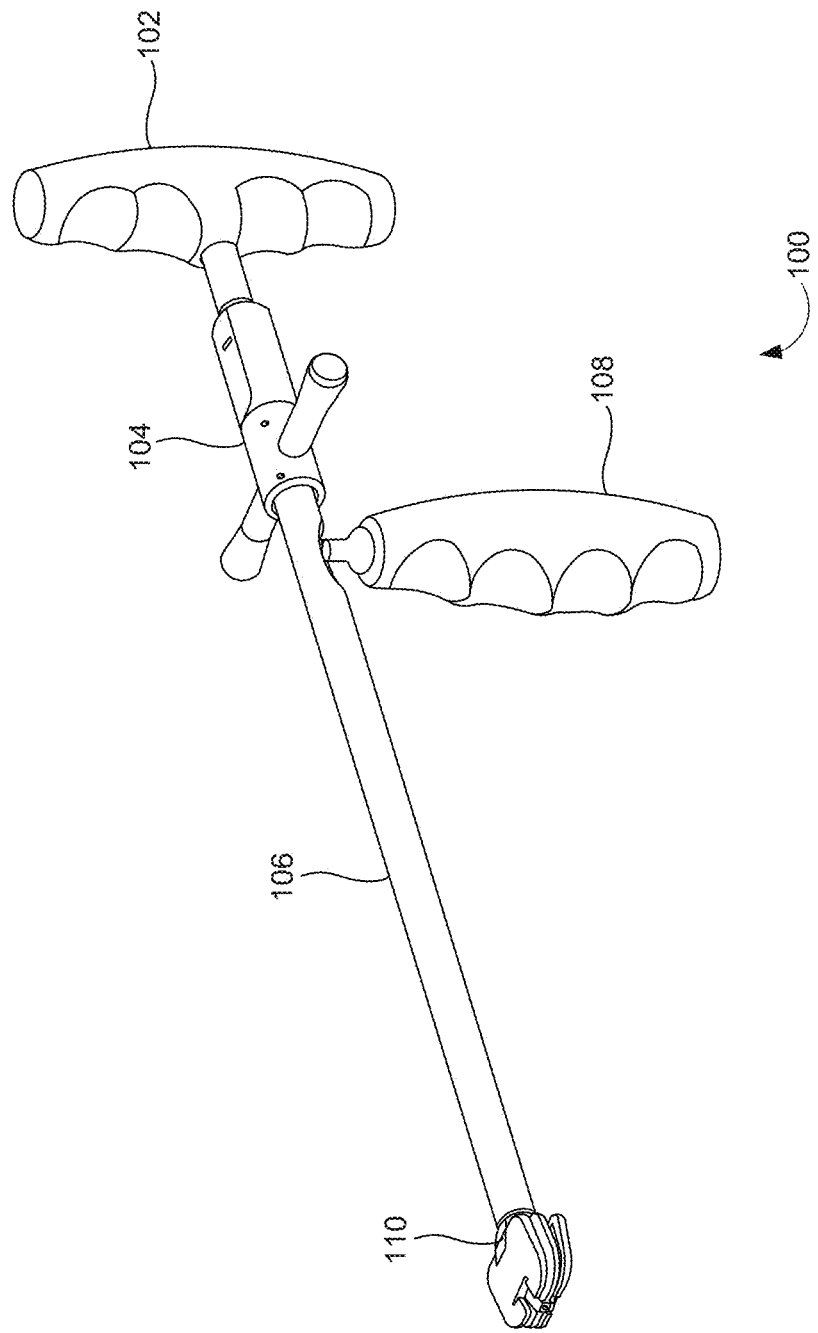
FIG. 1 illustrates a perspective view of an interbody distractor trial assembly according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a distractor trial assembly that allows a user to distract the disc space to various heights and measure an angle of lordosis/kyphosis for proper sizing and choice of matching interbody implants. The embodiments herein achieve this by providing an interbody distractor trial assembly that measures a height and an angle of the interbody distractor trial assembly when a height handle and a wedge sleeve knob are actuated (e.g., linearly or by rotation, etc.). Further it allows the user to distract the disc space to various heights and then measure an angle of lordosis/kyphosis for proper sizing and choice of matching interbody implants. Referring now to the drawings, and more particularly to FIGS. 1 through 8, where similar reference characters denote corresponding features consistently throughout the figures, there are shown preferred embodiments.

FIG. 1 illustrates a perspective view of an interbody distractor trial assembly 100 according to an embodiment herein. The interbody distractor trial assembly 100 includes a height handle 102, a wedge sleeve knob 104, a wedge sleeve 106, a main handle 108, and an expansion head 110. The height handle 102 measures a height of the interbody distractor trial assembly 100 when a portion of the interbody distractor trial assembly 100 is positioned in a vertebral body (not shown).

The wedge sleeve knob 104 is positioned between the height handle 102 and the wedge sleeve 106. The wedge sleeve knob 104 drives the wedge sleeve 106 linearly towards the vertebral body when the wedge sleeve knob 104 is actuated by rotating in at least one direction (e.g., a clockwise direction) or moved linearly in another embodiment.

The main handle 108 is coupled to the middle main shaft 236 to provide a grip or support to a user. The expansion head 110 is coupled to the middle main shaft 236. The expansion head 104 is positioned in the vertebral body, in one embodiment. The wedge sleeve 106 controls the angle of the expansion head 110 when the wedge sleeve 106 interacts with the expansion head 110. The height handle 102 controls the height of the expansion head 110 when turned. A height of the expansion head 110 and an angle of surface plates of the expansion head 110 are measured when the height handle 102 and the wedge sleeve knob 104 are actuated (e.g., rotation, linear translation, etc.).

Figure 2:
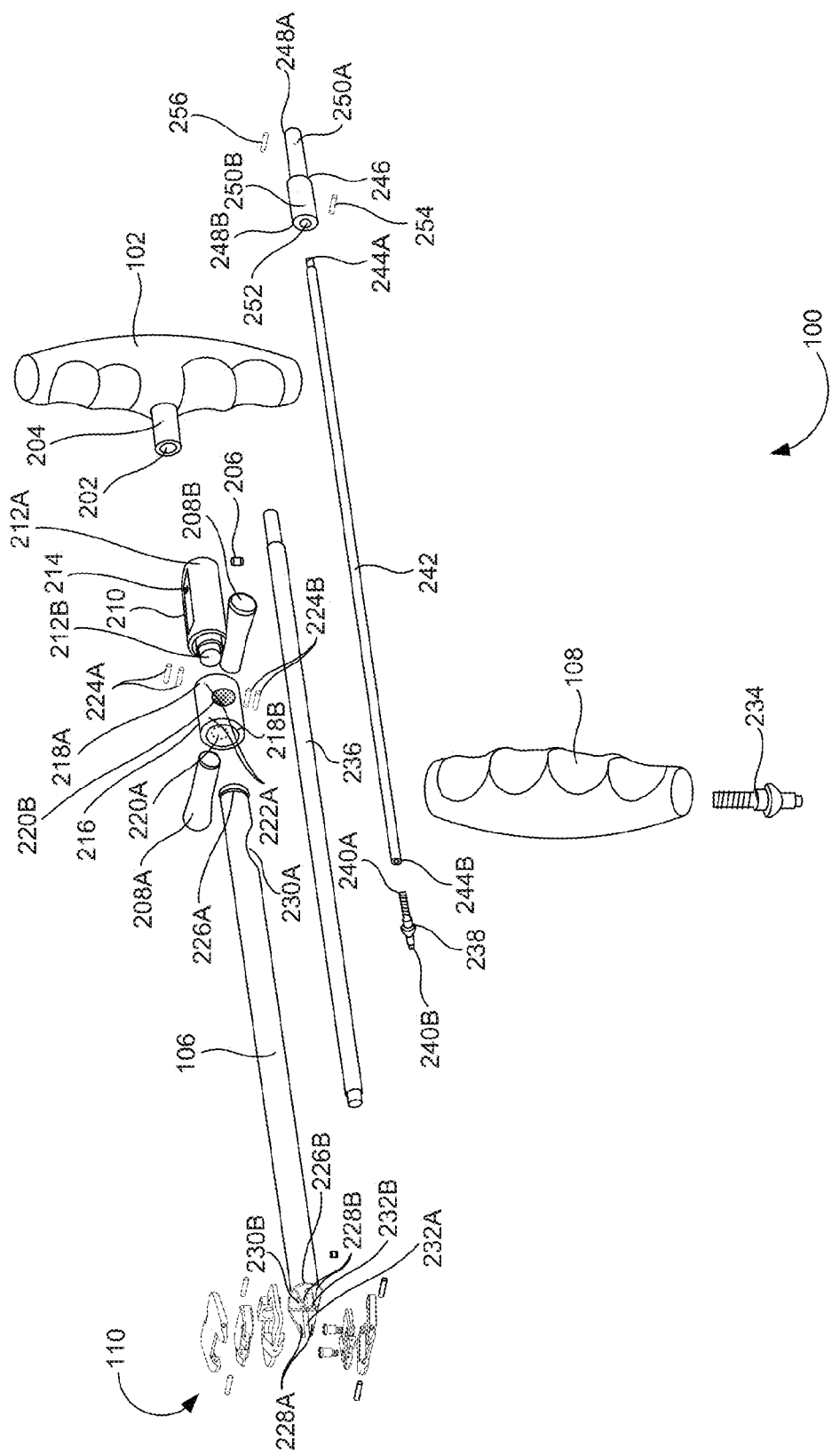
FIG. 2 illustrates an exploded view of the interbody distractor trial assembly of FIG. 1 according to an embodiment herein.

FIG. 2 illustrates an exploded view of the interbody distractor trial assembly 100 of FIG. 1 according to an embodiment herein. The interbody distractor trial assembly 100 includes the height handle 102, the wedge sleeve knob 104, the wedge sleeve 106, the main handle 108, and the expansion head 110. The height handle 102 includes a hole 202 and a receptacle 204. The wedge sleeve knob 104 includes a clocking pin 206, a first arm 208A, a second arm 208B, a gauge sleeve 210 having a first end 212A, a second end 212B, a clocking pin holder 214, a wedge sleeve knob housing 216 having a first end 218A, a second end 218B, a first slot 220A, a second slot 220B, a first pair of receptacles 222A, a first pair of cross pins 224A, and a second pair of cross pins 224B. The wedge sleeve knob housing 104 may further include a second pair of receptacles 222B (not shown in FIG. 2). The wedge sleeve 106 includes a first end 226A, a second end 226B having a first pair of arms 228A and a second pair of arms 228B. The wedge sleeve 106 further includes (i) a first slot 230A in close proximity to the first end 226A, (ii) a second slot 230B in close proximity to the second end 226B, the first pair of arms 228A, and the second pair of arms 228B. The first pair of arms 228A includes a first slot 232A. The second pair of arms 228B includes a second slot 232B. The main handle 108 includes a handle fitting component 234. The interbody distractor trial assembly 100 further includes a middle main shaft 236, a cam head 238 having a first end 240A and a second end 240B, an inner cam shaft 242 having a first end 244A and a second end 244B, a cam shaft fitting 246 having a first end 248A that includes a first receptacle 250A on a surface of the first end 248A, a second end 248B that includes a second receptacle 250B on a surface of the second end 248B and a hole 252, a cross pin 254, and a handle cross pin 256.

The height handle 102 connects to the cam shaft fitting 246, the inner cam shaft 242, and the cam head 238. The height handle 102, the inner cam shaft 242, and the cam head 238 is inside the middle main shaft 236. The height handle 102 adjusts a height of the interbody distractor trial assembly 100 in one or more directions. The height may be adjusted (e.g., increased or decreased) by actuating the height handle 102 by rotation in either a clockwise direction or an anti-clockwise direction or by linear translation in another embodiment. The wedge sleeve knob 104 is positioned between the height handle 102 and the wedge sleeve 106. The wedge sleeve knob 104 drives the wedge sleeve 106 linearly towards the vertebral body when the wedge sleeve knob 104 is actuated (e.g., rotation or linear translation, etc.).

The wedge sleeve 106 is positioned between the wedge sleeve knob 104 and the expansion head 110. The wedge sleeve 106 controls an angle of the surface plates of the expansion head 110 when the wedge sleeve 106 interacts with the expansion head 110. The main handle 108 is fitted through the first slot 230A, to the middle main shaft 236, using the handle fitting component 234. The main handle 108 is adapted to provide a support/grip to the user. The expansion head 110 distracts a disc space and associated ligamentous tissues in the vertebral body to correct a spinal deformity and for easier insertion of an implant in the vertebral body.

The hole 202 is coupled to the first end 248A of the cam shaft fitting 246. The receptacle 204 receives the handle cross pin 256 to lock the first end 248A of the cam shaft fitting 246 with the hole 202. The first arm 208A and the second arm 208B accommodate in the first slot 220A and the second slot 220B of the wedge sleeve knob housing 216. The first end 212A of the gauge sleeve 210 engages/receives the cam shaft fitting 246. The second end 212B of the gauge sleeve 210 is fitted in the first end 218A of the wedge sleeve knob housing 216. The clocking pin holder 214 receives the clocking pin 206 such that the clocking pin 206 locks the middle main shaft 236 with the gauge sleeve 210. The wedge sleeve housing 216 accommodates the first arm 208A, the second arm 208B, the second end 212B of the gauge sleeve 210, and the first end 226A of the wedge sleeve 106. The assembly of the wedge sleeve 106, the wedge sleeve housing 216, and the gauge sleeve 210 can linearly translate by a threaded mechanism over the middle main shaft 236.

The first pair of receptacles 222A accommodates the first pair of cross pins 224A. The second pair of receptacles (not shown in FIG. 1B) accommodates the second pair of cross pins 224B such that the first pair of cross pins 224A and the second pair of cross pins 224B link the wedge sleeve 106 to the wedge sleeve knob housing 216 to the gauge sleeve 104. The second slot 230B accommodates the middle main shaft 236, the cam head 238 having the first end 240A and the second end 240B, the inner cam shaft 242 having the first end 244A and the second end 244B such that the cam head 238 is assembled coaxial with the inner cam shaft 242. The first slot 232A of the first pair of arms 228A and the second slot 232B of the second pair of arms 228B accommodate a portion of the expansion head 110.

The first end 248A of the cam shaft fitting 246 engages the hole 202 of the height handle 102. The second end 248B of the cam shaft fitting 246 engages the first end 244A of the inner cam shaft 242. The first receptacle 250A receives the handle cross pin 256 such that the first end 248A of the cam shaft fitting 246 locks with the height handle 102. Similarly, the second receptacle 250B receives the cross pin 258 such that the second end 248B of the cam shaft fitting 246 and the first end 244A of the inner cam shaft 242 are locked together.

Figure 3B:
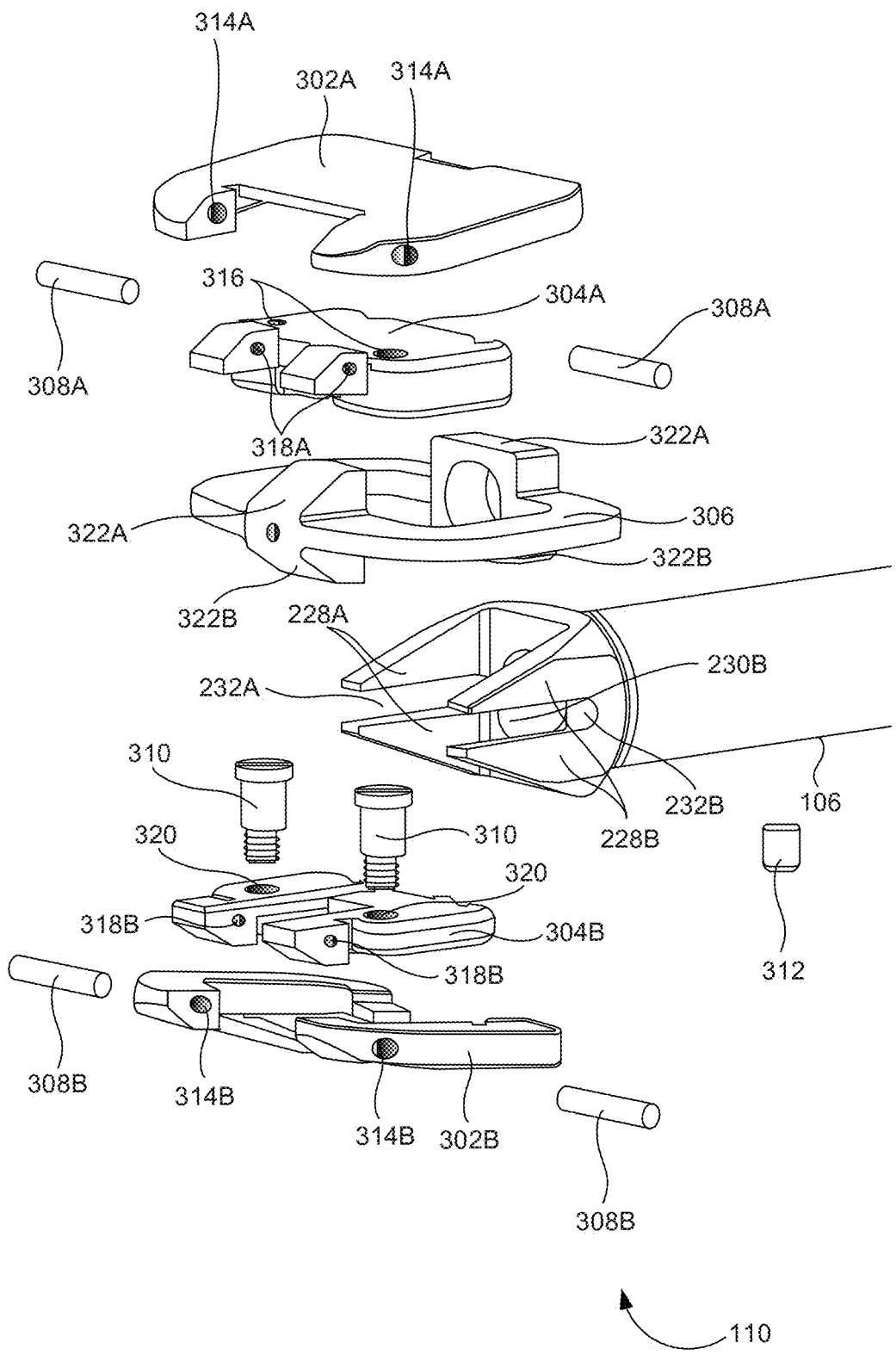
FIG. 3B illustrates an exploded view of the expansion head of the interbody distractor trial assembly of FIG. 1 according to an embodiment herein.

FIG. 3A illustrates the expansion head 104 of the interbody distractor trial assembly 100 of FIGS. 1 and 2 according to an embodiment herein. FIG. 3B illustrates an exploded view of the expansion head 110 of the interbody distractor trial assembly 100 of FIGS. 1 and 2 according to an embodiment herein. The expansion head 110 includes a first surface plate 302A, a second surface plate 302B, a first lifter 304A, a second lifter 304B, a head frame body 306, a first pair of hinge pins 308A, a second pair of hinge pins 308B, a pair of assembly screws 310, and a clocking pin 312. The first surface plate 302A includes a first pair of hinge holders 314A. The second surface plate 302B includes a second pair of hinge holders 314B. The first lifter 304A includes a first pair of assembly screw holders 316, and a first pair of hinge slots 318A. The second lifter 304B includes a second pair of hinge slots 318B and a pair of assembly screw holders 320. The head frame body 306 includes a top extension 322A, and a bottom extension 322B.

The first surface plate 302A is mounted on a top surface of the first pair of arms 228A and the second pairs of arms 228B such that an inner surface of the first surface plate 302A accommodates a top portion of the first lifter 304A. Similarly, the second surface plate 302B is mounted on a bottom surface of the first pair of arms 228A and the second pairs of arms 228B such that an inner surface of the second surface plate 302B accommodates the a bottom portion of the second lifter 304B.

The first lifter 304A and the second lifter 304B lift the first surface plate 302A and the second surface plate 302B respectively. The head frame body 306 accommodates a bottom portion of the first lifter 304A, and a top portion of the second lifter 304B. The first pair of hinge pins 308A fit in the first pair of hinge holders 314A and the first pair of hinge slots 318A such that the first surface plate 302A and the first lifter 304A are locked together. The second pair of hinge pins 308B fit in the second pair of hinge holders 314B and the second pair of hinge slots 318B such that the second surface plate 302B and the second lifter 304B are locked together. The pair of assembly screws 310 locks the second lifter 304B with the second surface plate 302B.

Each of the first surface plate 302A, the second surface plate 302B, the first lifter 304A, and the second lifter 304B may include an opening that is adapted to accommodate the top extension 322A of the head frame body 306 and the bottom extension 322B of the head frame body 306 such that they are locked together. With respect to FIGS. 2 through 3B, the middle main shaft 236 fits in a cylindrical portion of the wedge sleeve 106. The first end 240A of the cam head 238 engages the second end 244B of the inner cam shaft 242. The second end 240B of the cam head 238 engages the expansion head 110 such that when the height handle 102 is actuated, the inner cam shaft 242 enables the second end 240B of the cam head 238 to drive the first lifter 304A (e.g., a top lifter) and the second lifter 304B (e.g., a bottom lifter) to lift the first surface plate 302A (e.g., a top surface angle plate), and the second surface plate 302B (e.g., a bottom surface angle plate) respectively. This allows measuring an angle of the first surface plate 302A, and the second surface plate 302B.

The first pair of hinge pins 308A tightens and/or provides support to the first surface plate 302A and the top lifter 304A, such that the first surface plate 302A and the top lifter 304A are held firmly with the head frame body 306. Similarly, the pair of assembly screws 320 and the second pair of hinge pins 308B tighten and/or provide support to the second surface plate 302B and the bottom lifter 304B, such that the second surface plate 302B and the bottom lifter 304B are held assembled with the head frame body 306.

Figure 4:
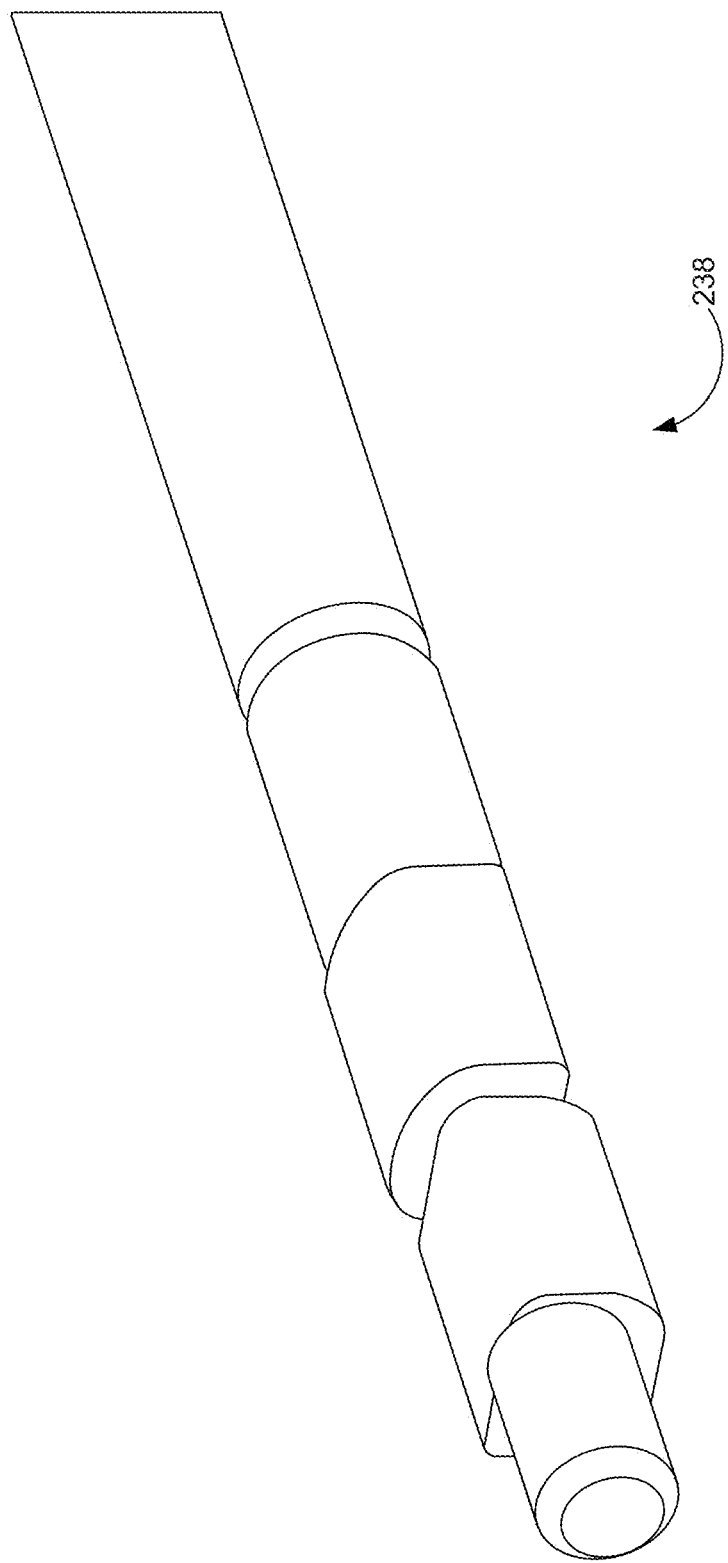
FIG. 4 illustrates a perspective view of the cam head that is co-axial assembled to the inner cam shaft according to an embodiment herein.

FIG. 4, with reference to FIG. 2 illustrates a perspective view of the cam head 238 that is co-axial assembled to the inner cam shaft 242 according to an embodiment herein.

Figure 5A:
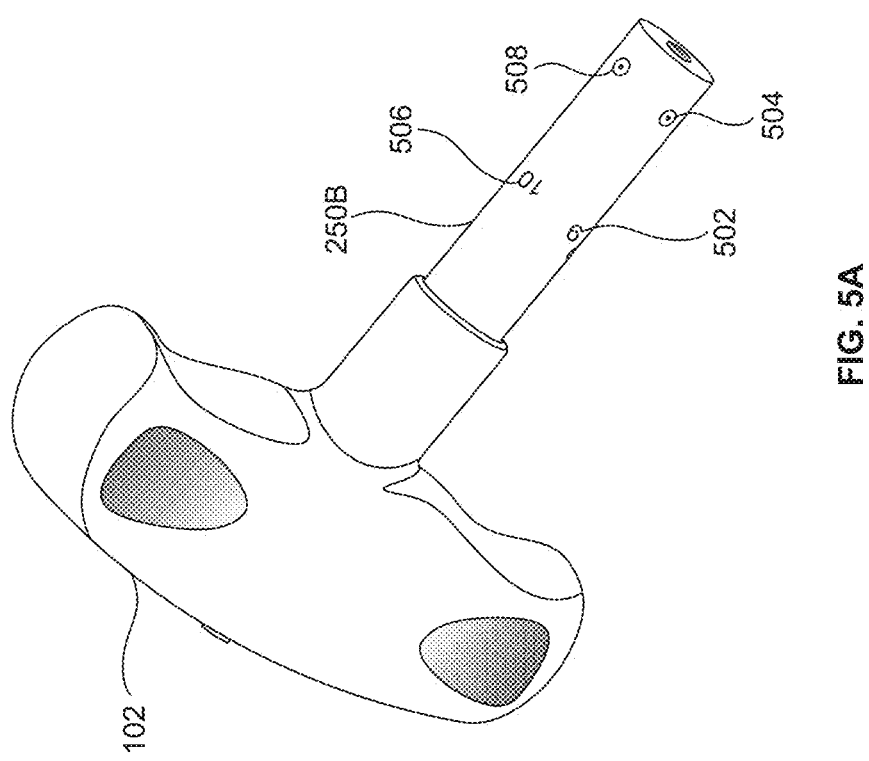
FIG. 5A illustrates a perspective view of the height handle coupled to the gauge sleeve having a first marker corresponding to a first reading dot, and a second marker corresponding to a second reading dot on the surface of the gauge sleeve according to an embodiment herein.
Figure 5C:
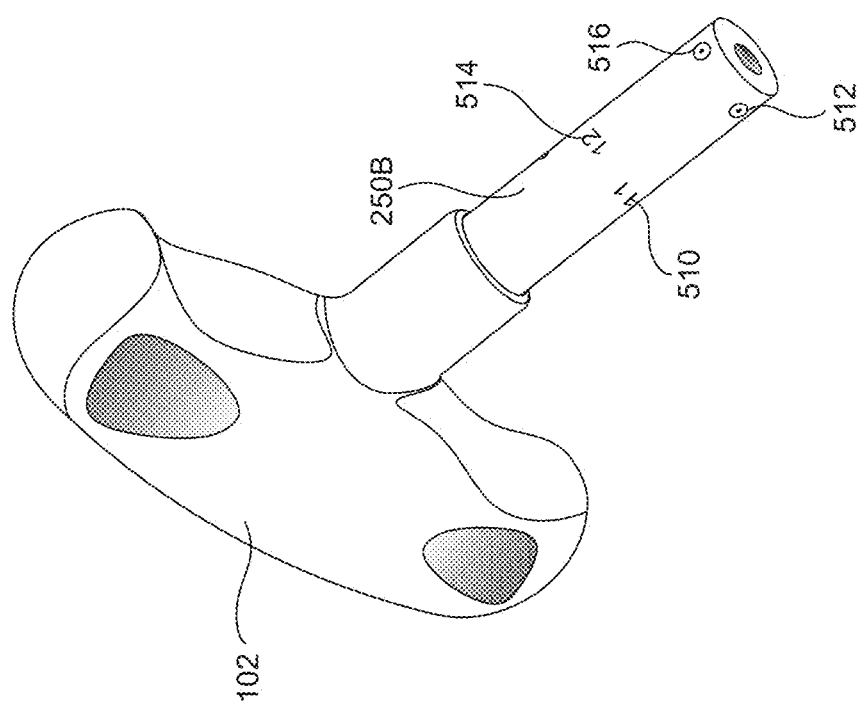
FIG. 5C illustrates a perspective view of the height handle coupled to the gauge sleeve having the third marker corresponding to the third reading dot 512 and a fourth marker corresponding to a fourth reading dot on the surface of the gauge sleeve according to an embodiment herein.

FIG. 5A through 5C illustrates a perspective view of the height handle 102 coupled to the second receptacle 250B having one or more markers according to an embodiment herein. In particular, FIG. 5A illustrates a perspective view of the height handle 102 coupled to the second receptacle 250B having a first marker 502 (e.g., 9) corresponding to a first reading dot 504, and a second marker 506 (e.g., 10) corresponding to a second reading dot 508 according to an embodiment herein. FIG. 5B illustrates a perspective view of the height handle 102 coupled to the second receptacle 250B having the second marker 506 (e.g., 10) corresponding to the second reading dot 508 and a third marker 510 (e.g., 11) corresponding to a third reading dot 512 according to an embodiment herein. FIG. 5C illustrates a perspective view of the height handle 102 coupled to the second receptacle 250B having the third marker 510 (e.g., 11) corresponding to the third reading dot 512 and a fourth marker 514 (e.g., 12) corresponding to a fourth reading dot 516 according to an embodiment herein. The first marker 502, the second marker 506, the third marker 510, and the fourth marker 514 are visible when the gauge sleeve 210 (shown in FIGS. 6A through 6C) is actuated in one or more directions (e.g., a clockwise direction, and/or an anti-clockwise direction or linear translation in another embodiment). The first marker 502, the second marker 506, the third marker 510, and the fourth marker 514 indicate a linear translation of the wedge sleeve 106. The first reading dot 504, the second reading dot 508, the third reading dot 512, and the fourth reading dot 516 are an angle reading dot, in one example embodiment.

Figure 6A:
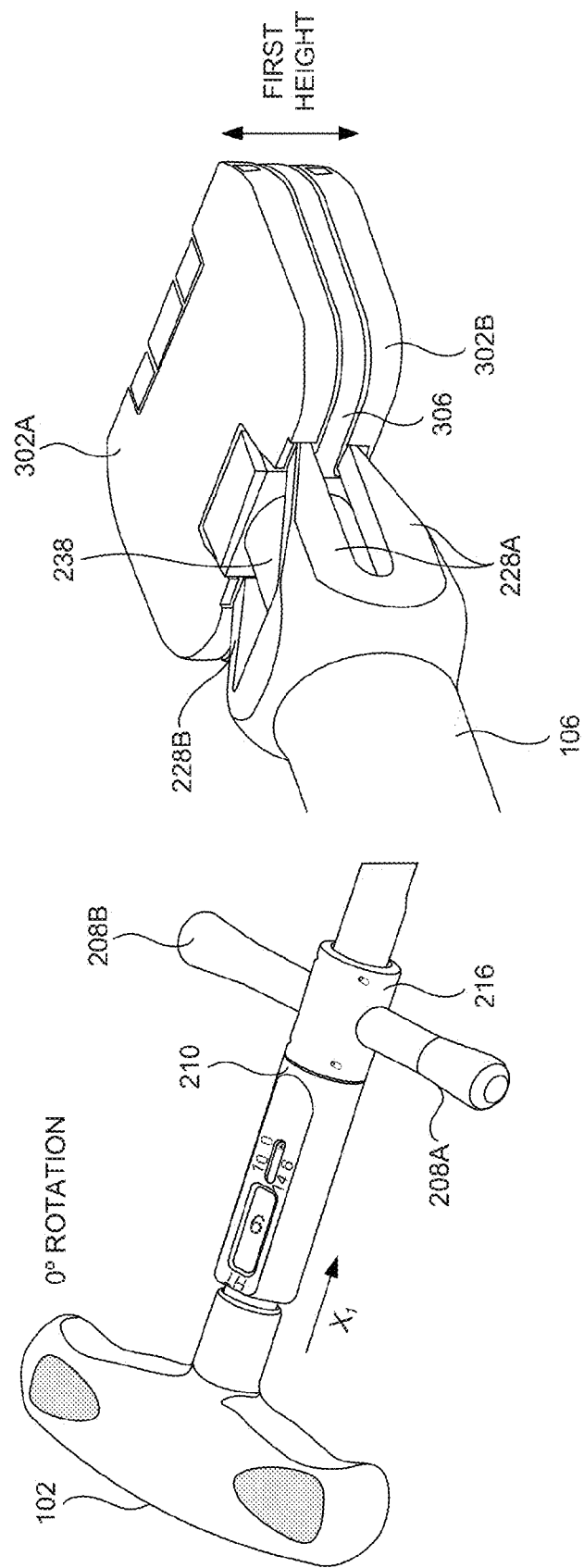
FIG. 6A illustrates a first height displacement of the expansion head and a first position of the wedge sleeve knob when the height handle is at a first angle according to an embodiment herein.

FIGS. 6A through 6D, with reference to FIGS. 1 through 5C illustrates perspective views of the height handle 102 coupled to the gauge sleeve 210 and the expansion head 110 according to an embodiment herein. FIGS. 6A through 6D further illustrates a comparison of an end of the gauge sleeve 210 with respect to an end of the expansion head 110. In particular, FIG. 6A illustrates a first height displacement of the expansion head 110 and a first position of the wedge sleeve knob 104 when the height handle 102 is at a first angle according to an embodiment herein. The first height displacement of the expansion head 110 is 9 mm (in one example embodiment, although other heights are possible in accordance with the embodiments herein) and the wedge sleeve knob 104 linearly translates to a first position X1 when the height handle 102 is at an angle of zero (0) degree (e.g., the first angle), in one example embodiment.

FIG. 6B illustrates a second height displacement of the expansion head 110 and a second position of the wedge sleeve knob 104 when the height handle 102 is at a second angle according to an embodiment herein. The second height displacement of the expansion head 110 is 10 mm (in one example embodiment, although other heights are possible in accordance with the embodiments herein) and the wedge sleeve knob 104 linearly translates to the second position X2 such that the second position X2 is greater than the first position X1, when the height handle 102 is at an angle of ninety (90) degree (e.g., the second angle), in another example embodiment.

Figure 6C:
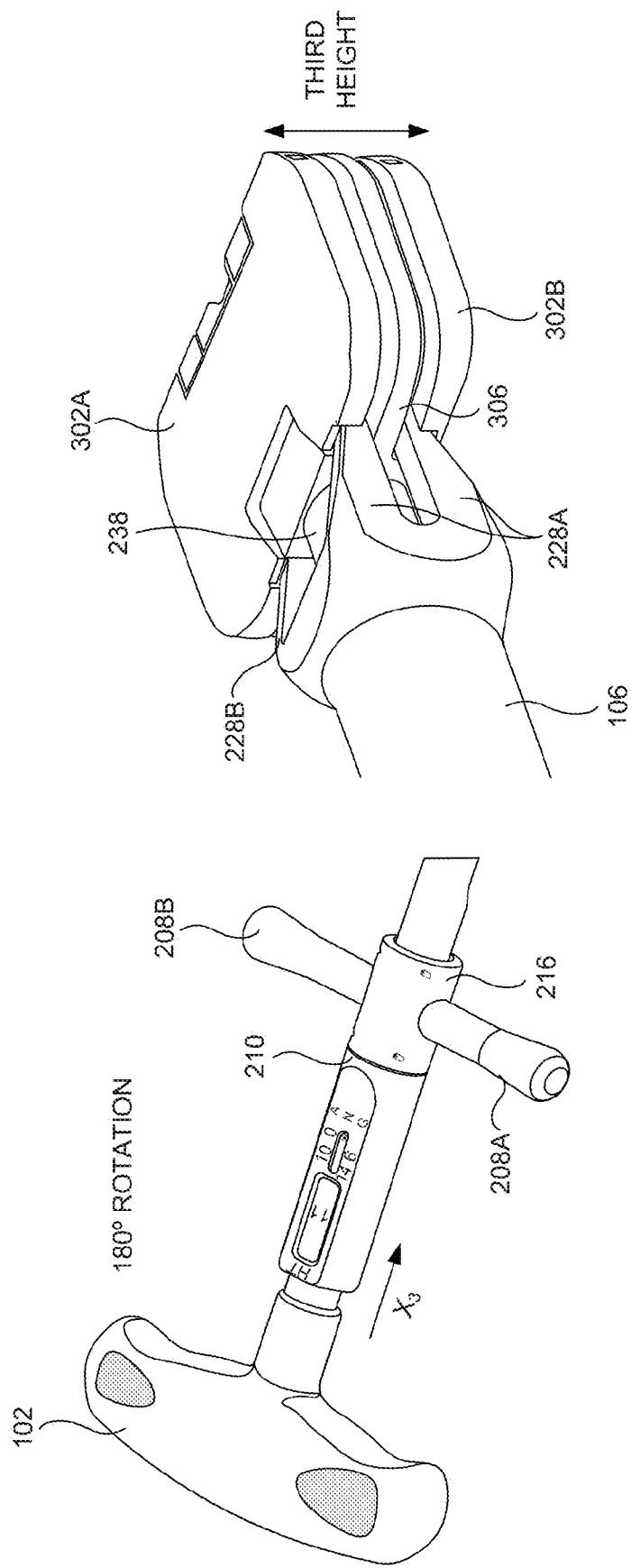
FIG. 6C illustrates a third height displacement of the expansion head and a third position of the wedge sleeve knob when the height handle is at a third angle according to an embodiment herein.

FIG. 6C illustrates a third height displacement of the expansion head 110 and a third position of the wedge sleeve knob 104 when the height handle 102 is at a third angle according to an embodiment herein. The second height displacement of the expansion head 110 is 11 mm (in one example embodiment, although other heights are possible in accordance with the embodiments herein) and the wedge sleeve knob 104 linearly translates to the third position X3 such that the third position X3 is greater than the second position X2, when the height handle 102 is at an angle of one hundred and eighty (180) degree (e.g., the third angle), in yet example embodiment.

Figure 6D:
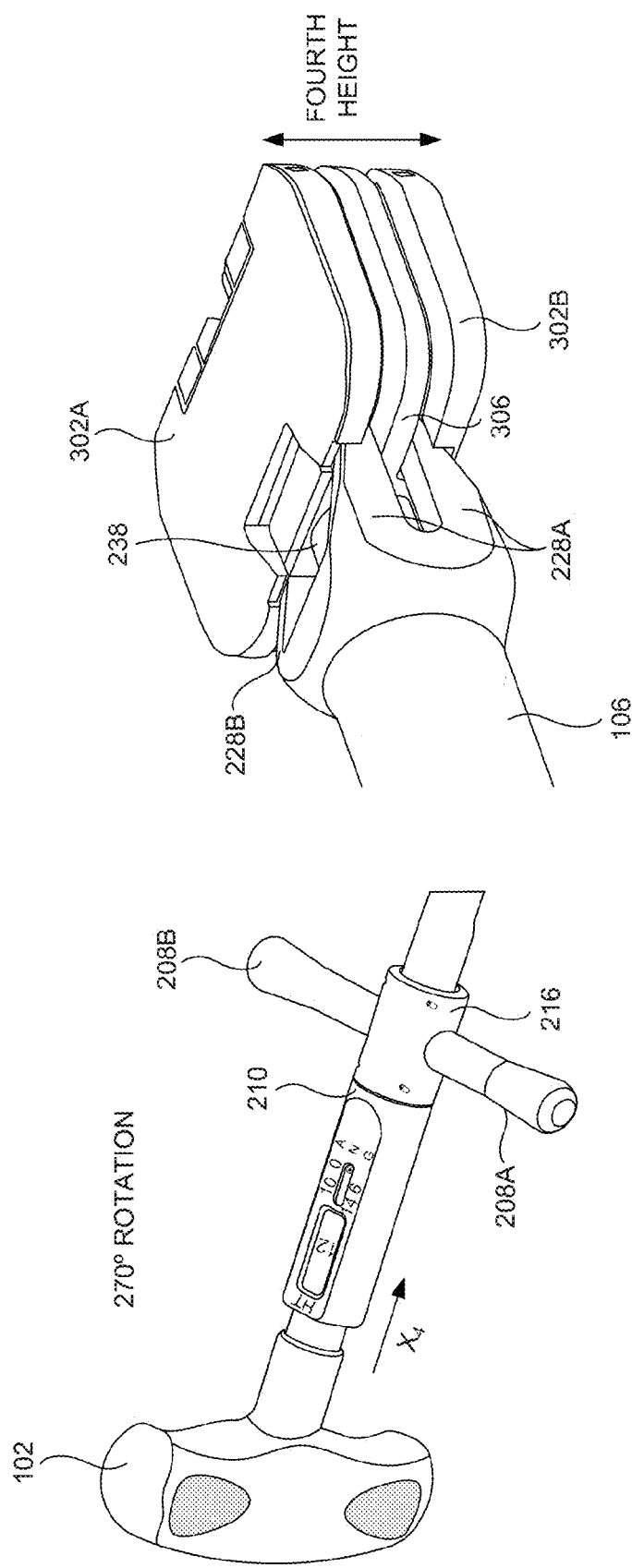
FIG. 6D illustrates a fourth height displacement of the expansion head and a fourth position of the wedge sleeve knob when the height handle is at a fourth angle according to an embodiment herein.

FIG. 6D illustrates a fourth height displacement of the expansion head 110 and a fourth position of the wedge sleeve knob 104 when the height handle 102 is at a fourth angle according to an embodiment herein. The fourth height displacement of the expansion head 110 is 12 mm (in one example embodiment, although other heights are possible in accordance with the embodiments herein) and the wedge sleeve knob 104 linearly translates to the fourth position X4 such that the fourth position is greater than the third position X3, when the height handle 102 is at an angle of two hundred and seventy (270) degree (e.g., the fourth angle), in another example embodiment. X4>X3>X2>X1, in one example embodiment. The first angle, the second angle, the third angle, and the fourth angle are separated by 90 degree interval, in one example embodiment. The calibrated position of the one or more markers (e.g., the first marker 502, the second marker 506, the third marker 510, and the fourth marker 514) and the corresponding angle reading dots (e.g., the first reading dot 504, the second reading dot 508, the third reading dot 512, and the fourth reading dot 516) are positioned accordingly such that they can be through a windows of the gauge sleeve 210 which is attached to and translates linearly with the advancement of the wedge sleeve knob 104.

The one or more markers and the corresponding angle reading dots are prepositioned and calibrated to be associated with the position of the height handle 102, in one example embodiment. When the wedge sleeve knob 104 advances further from its start position causing the first surface plate 302A and the second surface plate 302B to angle open, the angle reading dots (that are fixed position on the height handle 102) are shown through the cutouts in the gauge sleeve 210 next to a different number associated with an appropriate angle measurement. The height handle 102 is connected to the inner shaft 242 as the cam head 238 adjusts the height of the expansion head 110 by raising the top lifter 304A and the bottom lifter 304B.

The first surface plate 302A and the second surface plate 302A are attached to the top lifter 304A and the bottom lifter 304B by the first pair of hinge holders 314A, the second pair of hinge holders 314B, the first pair of hinge slots 318A, and the second pair of hinge slots 318B using the first pair of hinge pins 308A and the second pair of hinge pins 308B, which allows different angle positions when the wedge sleeve 106 pushes them open as the wedge sleeve knob 104 is turned and advanced. The first surface plate 302A, the second surface plate 302B, the first lifter 304A, the second lifter 304B, the head frame body 306 freely float and can change height and angle. The cam head 238 is exposed inside the expansion head 110 such that the cam head 238 makes contact with the first lifter 304A and the second lifter 304B to provide the height adjustment. The first end 226A and the second end 226B of the wedge sleeve 106 change an angle position of the first surface plate 302A and the second surface plate 302B, which are connected to the first lifter 304A and the second lifter 304B.

Figure 7A:
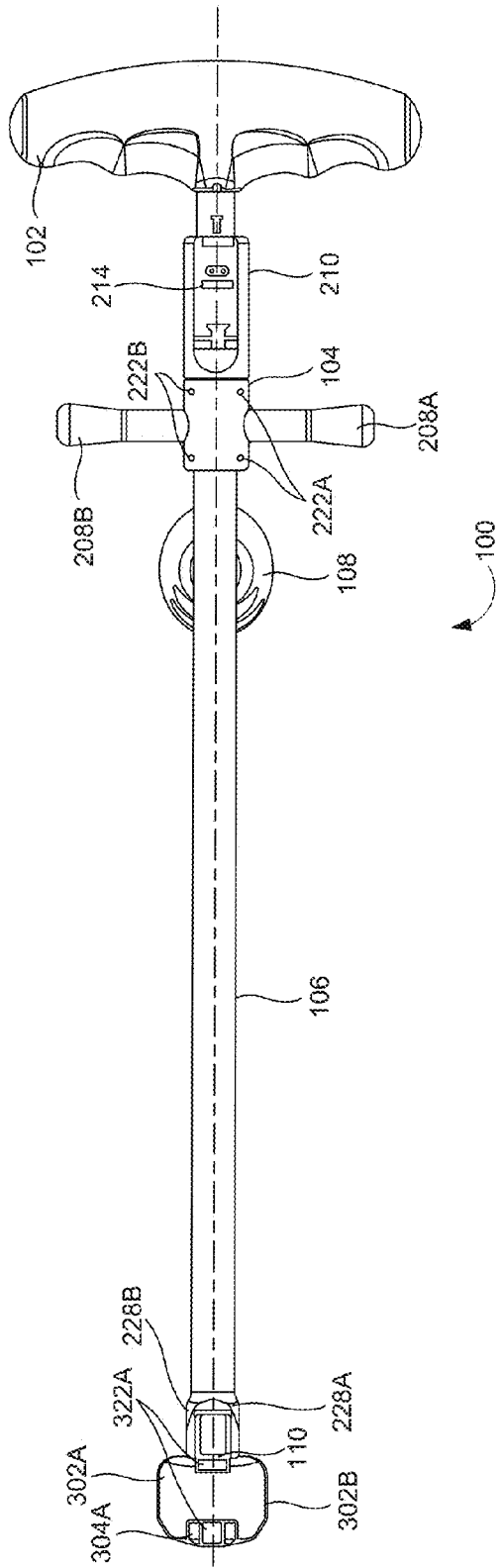
FIG. 7A illustrates a top view of the interbody distractor trial assembly of FIG. 1 according to an embodiment herein.
Figure 7B:
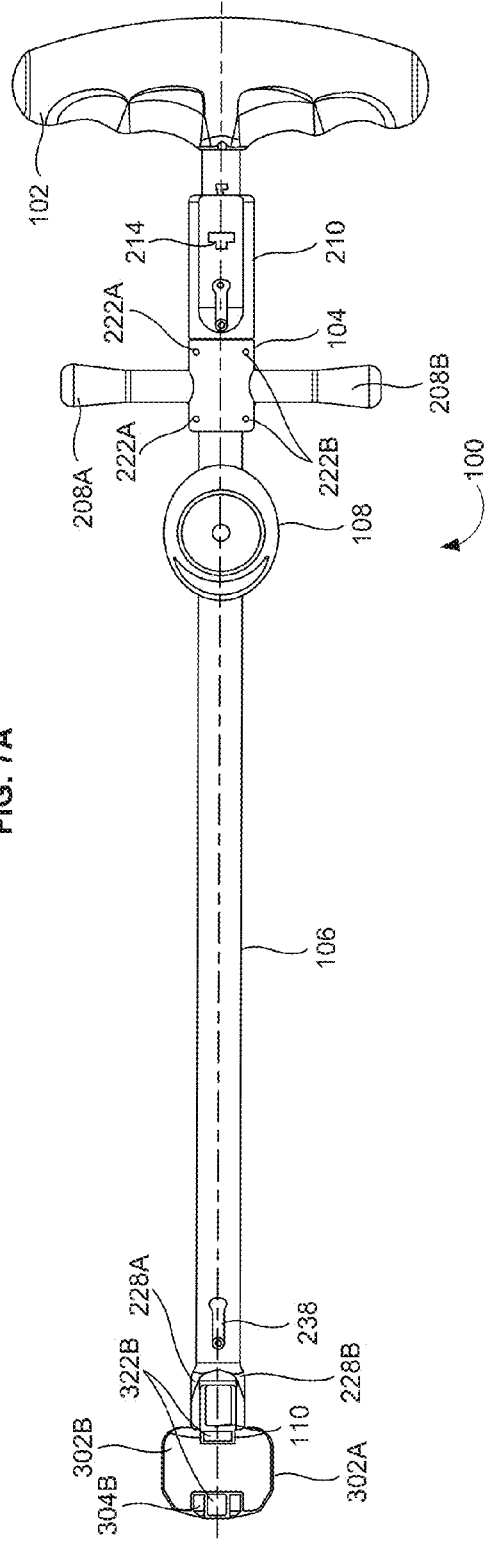
FIG. 7B illustrates a bottom view of the interbody distractor trial assembly of FIG. 1 according to an embodiment herein.
Figure 7C:
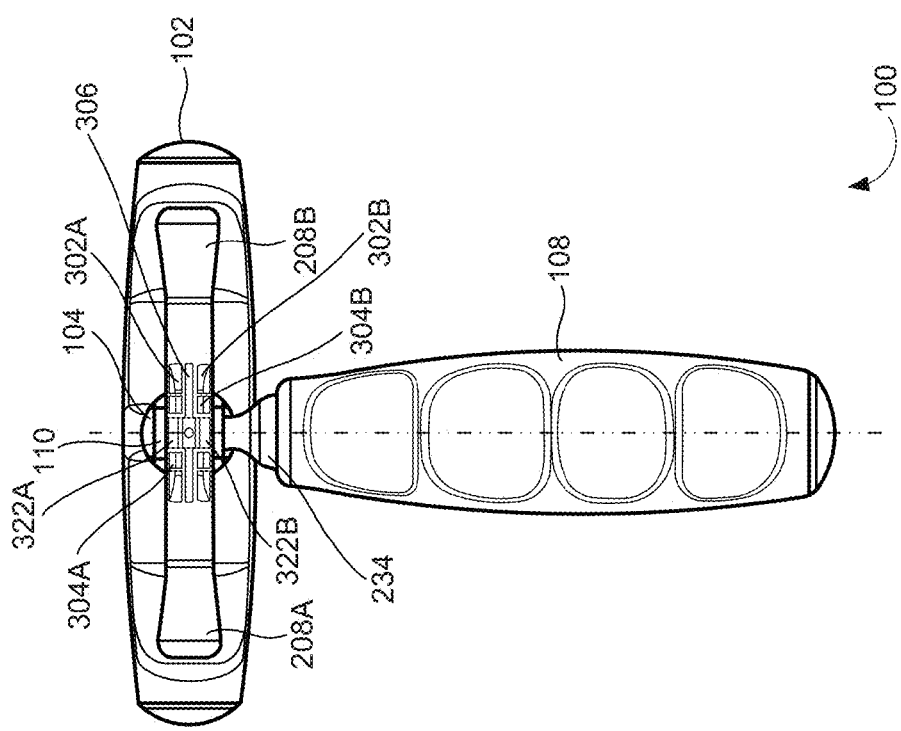
FIG. 7C illustrates a rear view of the interbody distractor trial assembly of FIG. 1 according to an embodiment herein.
Figure 7D:
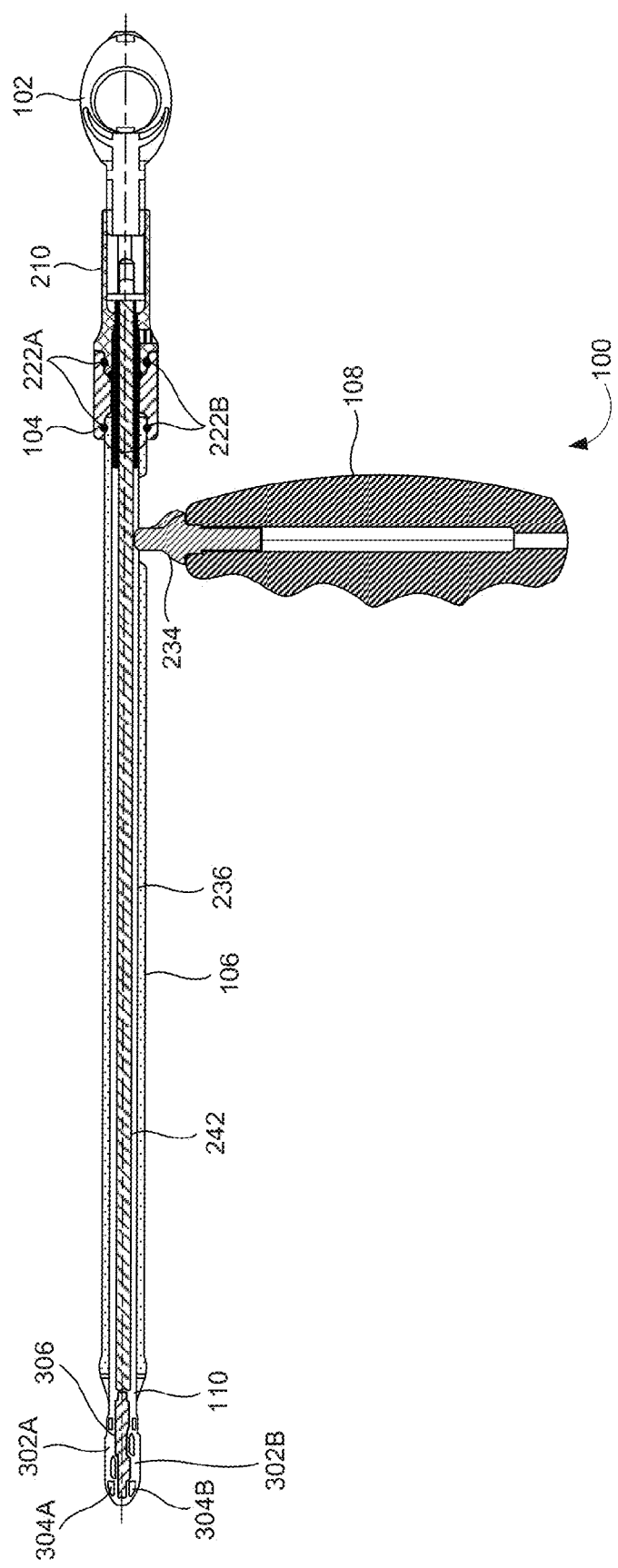
FIG. 7D illustrates a sectional view of the interbody distractor trial assembly of FIG. 1 according to an embodiment herein.

FIGS. 7A through 7D illustrates a top view, a bottom view, a rear view, and a sectional view of the interbody distractor trial assembly 100 of FIG. 1 according to an embodiment herein. In particular, FIG. 7A illustrates a top view of the interbody distractor trial assembly 100 of FIG. 1 according to an embodiment herein. FIG. 7B illustrates a bottom view of the interbody distractor trial assembly 100 of FIG. 1 according to an embodiment herein. FIG. 7C illustrates a rear view of the interbody distractor trial assembly 100 of FIG. 1 according to an embodiment herein. FIG. 7D illustrates a sectional view of the interbody distractor trial assembly 100 of FIG. 1 according to an embodiment herein. The top view, the bottom view, and the sectional view of the interbody distractor trial assembly 100 includes the second pair of receptacles 222B which is not shown in FIG. 2.

Figure 8:
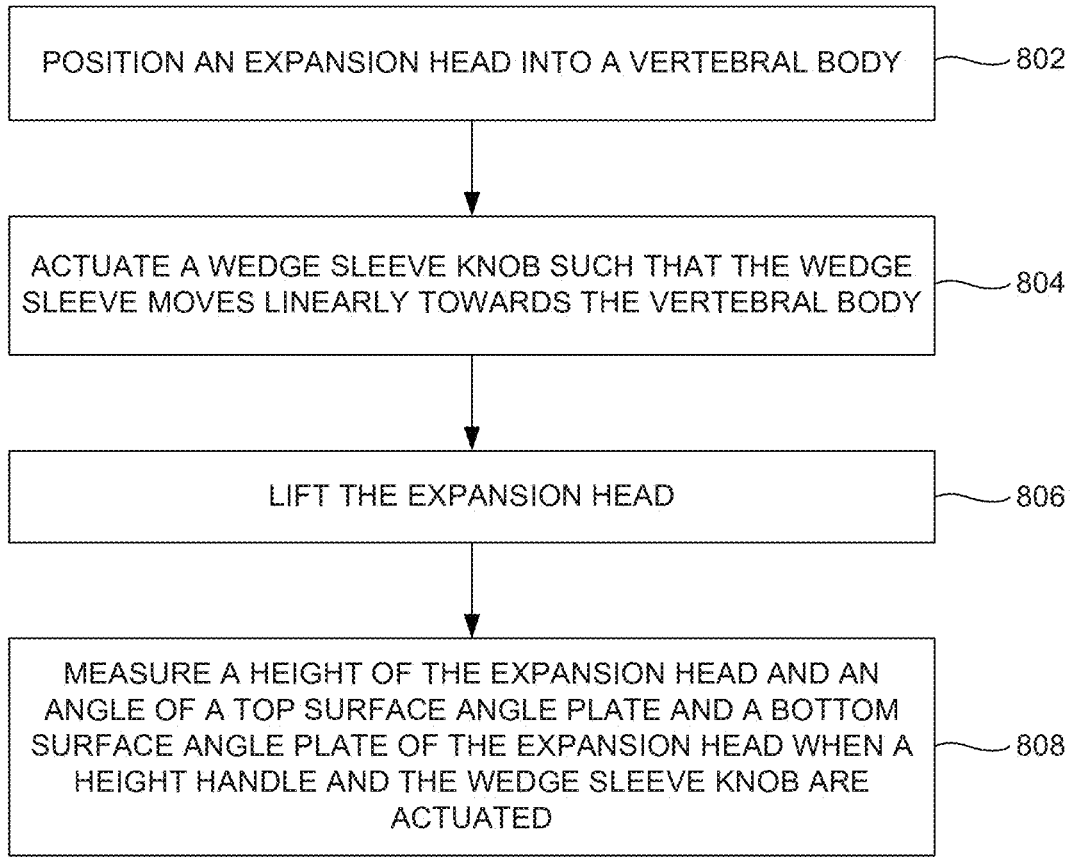
FIG. 8 is a flow diagram illustrating a method of operating an interbody device to measure a height and an angle for an associated implant according to an embodiment herein.

FIG. 8, with reference to FIGS. 1 through 7D, is a flow diagram illustrating a method of operating an interbody device to measure a height and an angle for an associated implant according to an embodiment herein. In one embodiment, the interbody device is the interbody distractor trial assembly 100 of FIGS. 1 and 2. The interbody device 100 includes the height handle 102, the wedge sleeve knob 104 coupled to the height handle 102, the wedge sleeve 106 coupled to the wedge sleeve knob 104, and the expansion head 110 coupled to the wedge sleeve 106. The expansion head 110 includes a top surface angle plate (e.g., the first surface plate 302A) and a bottom surface angle plate (e.g., the second surface plate 302B). In step 802, the expansion head 110 is positioned into the vertebral body. In step 804, the wedge sleeve knob 104 is actuated such that the wedge sleeve 106 moves linearly towards the vertebral body. In step 806, the expansion head 110 is lifted. In step 808, a height of the expansion head 110 and an angle of the top surface angle plate 302A and the bottom surface angle plate 302B of the expansion head 110 are measured when the height handle 102 and the wedge sleeve knob 104 are actuated.

A calibrated gauge marker may be positioned at each position of the height handle 102 and a corresponding height. The expansion head 110 further includes the head frame body 306 that is coupled to the top surface angle plate 302A and the bottom surface angle plate 302B. A top lifter (e.g., the first lifter 304A) may be positioned between the top surface angle plate 302A and the head frame body 306. A bottom lifter (e.g., the second lifter 304B) is positioned between the bottom surface angle plate 304B and the head frame body 306.

The expansion head 110 may be adjusted to a first height when (i) the height handle 102 is at a first angle, and (ii) the wedge sleeve knob translates to a first position as shown in FIG. 6A. The expansion head 110 may be adjusted to a second height when (i) the height handle 102 is at a second angle, and (ii) the wedge sleeve knob 104 translates to a second position as shown in FIG. 6B. The second position is greater than the first position, in one example embodiment.

The expansion head 110 may be adjusted to a third height when (i) the height handle 102 is at a third angle, and (ii) the wedge sleeve knob 104 translates to a third position. The third position is greater than the second position, in another example embodiment. The expansion head 110 may be adjusted to a fourth height when (i) the height handle 102 is at a fourth angle, and (ii) the wedge sleeve knob 104 translates to a fourth position. The fourth position is greater than the third position, in yet another embodiment.

The first angle, the second angle, the third angle, and the fourth angle are separated by a 90 degree interval. The expansion head 110 is adjusted to any of the first height, the second height, the third height, or the fourth height to enable at least one of (i) a distraction of disc space and associated ligamentous tissues, (ii) a correction of spinal deformity, and (iii) an easier insertion of the associated implant in the vertebral body.

The interbody distractor trial assembly 100 allows a user (e.g., a surgeon, a medical professional, or any person who is qualified to perform a surgical procedure, etc.) to distract the disc space to various heights and angles of lordosis/kyphosis and integrally measure such height and angle to determine proper sizing and choice of matching interbody implants. The interbody distractor trial assembly 100 combines multiple height trials, multiple angled trials, and a distractor into a single instrument for improved ease of use. The interbody distractor trial assembly 100 allows for soft tissue distraction, concurrently allowing the user to subsequently determine an optimal associated implant size through use of various size footprints that are capable of adjusting height and angle of geometry. Since, the distraction and size trialing can be done all at once, the interbody distractor trial assembly 100 further avoids the user having to pass multiple instruments by sensitive vascular and neural anatomy multiple times where damage to the anatomy may occur.

The interbody distractor trial assembly 100 may be used in an interbody spine surgery from an anterior, and also a lateral or posterior-lateral approach if so configured. The interbody distractor trial assembly 100 may be inserted once and sequentially distracted to a height followed by an angle measurement. The complex design of the interbody distractor trial assembly 100 allows using the height handle 102 connected to the cam shaft to change height combined with the second handle to change the angle and adjusts variable angle of the first surface plate 302A and the second surface plate 302B using the top lifter 304A and the bottom lifter 304B. The calibrated position of the one or more markers (e.g., the first marker 502, the second marker 506, the third marker 510, and the fourth marker 514) and the corresponding angle reading dots (e.g., the first reading dot 504, the second reading dot 508, the third reading dot 512, and the fourth reading dot 516) are positioned accordingly such that they can be through a window of the gauge sleeve 210 which is attached to and translates linearly with the advancement of the wedge sleeve knob 104.

The distractor trial assembly 100 may use various size footprints, heights, angle positions, more than one pair of internal cams, and various orientation of the height handle 102. The distractor trial assembly 100 further allows the user to perform various methods of controlling a linear position of the wedge sleeve 106 (e.g., other than threaded). Various gauge design and orientations may be determined in addition to the angle measurement.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An interbody distractor and geometry trial instrument to measure a height and an angle for an associated implant comprising:
   a height handle comprising a hole;
   a cam shaft fitting adapted to fit in said hole of said height handle, wherein said cam shaft fitting comprises a hole and a cross pin hole;
   a cross pin adapted to be fitted in said cross pin hole such that said cam shaft fitting firmly holds an inner cam shaft;
   an expansion head coupled to said height handle, wherein said expansion head comprises a first surface plate and a second surface plate, wherein said expansion head is adapted to be positioned in a vertebral body, wherein a thickness of said expansion head defines a height of said expansion head, and wherein said expansion head is adapted to be expanded by displacement of said first surface plate relative to said second surface plate causing a height of said expansion head to increase to one of a plurality of heights and causing said first surface plate to create an angle relative to said second surface plate;
   a wedge sleeve coupled to said expansion head, wherein said wedge sleeve controls an angle of said first surface plate and said second surface plate when said wedge sleeve interacts with said expansion head; and
   a wedge sleeve knob positioned between said height handle and said wedge sleeve, wherein said wedge sleeve knob is adapted to drive said wedge sleeve linearly towards said vertebral body when said wedge sleeve knob is actuated, and wherein said height of said expansion head and said angle of said first surface plate relative to said second surface plate are measured by a gauge sleeve coupled to said height handle to determine said height and said angle of said associated implant when said height handle and said wedge sleeve knob are actuated.

2. The interbody distractor of claim 1, wherein said wedge sleeve comprises a first pair of arms and a second pair of arms, wherein said first pair of arms comprises a first slot, and wherein said second pair of arms comprises a second slot.

3. The interbody distractor of claim 2, wherein said expansion head further comprises:
   a first clocking pin;
   a first lifter adapted to lift said first surface plate;
   a second lifter adapted to lift said second surface plate;
   a head frame body positioned between said first slot and said second slot of said first pair of arms and said second pair of arms of said wedge sleeve, wherein said head frame body is adapted to accommodate said first lifter and said second lifter;
   a first pair of hinge pins adapted to hold said second lifter and said second surface plate such that said first lifter and said first surface plate are held assembled with said head frame body; and
   a second pair of hinge pins adapted to hold said second lifter and said second surface plate.

4. The interbody distractor of claim 3, wherein said wedge sleeve knob comprises:
   a second clocking pin;
   a pair of arms adapted to advance said wedge sleeve linearly towards said vertebral body;
   said gauge sleeve comprising a first end and a second end, wherein said second end is positioned around said height handle, wherein said gauge sleeve is adapted to translate linearly towards said vertebral body when said pair of arms are actuated;
   a wedge sleeve knob housing adapted to accommodate said pair of arms, said first end of said gauge sleeve, and said wedge sleeve; and
   a pair of cross pins adapted to assemble said gauge sleeve and said wedge sleeve in said wedge sleeve knob housing.

5. The interbody distractor of claim 3, wherein said expansion head further comprises a pair of assembly screws adapted to capture said second lifter and said second surface plate such that the second lifter and said second surface plate are held assembled with said head frame body.

6. The interbody distractor of claim 1, wherein said expansion head is adapted to distract a disc space and associated ligamentous tissues in said vertebral body.

7. The interbody distractor of claim 1, further comprising:
   a second handle coupled to said wedge sleeve;
   a middle main shaft that is adapted to fit inside said wedge sleeve; and
   said inner cam shaft and a cam head that are adapted to fit inside said middle main shaft such that said cam head is assembled coaxial with said inner cam shaft, wherein said cam head adjusts said height of said expansion head and said angle of said first surface plate relative to said second surface plate when said height handle and said wedge sleeve knob are actuated.

8. The interbody distractor of claim 7, wherein said cam head adjusts said expansion head to a first height when (i) said height handle is at a first angle, and (ii) said wedge sleeve knob translates to a first position.

9. The interbody distractor of claim 8, wherein said cam head adjusts said expansion head to a second height when (i) said height handle is at a second angle, and (ii) said wedge sleeve knob translates to a second position, wherein said second position is greater than said first position.

10. The interbody distractor of claim 9, wherein said cam head adjusts said expansion head to a third height when (i) said height handle is at a third angle, and (ii) said wedge sleeve knob translates to a third position, wherein said third position is greater than said second position.

11. The interbody distractor of claim 10, wherein said cam head adjusts said expansion head to a fourth height when (i) said height handle is at a fourth angle, and (ii) said wedge sleeve knob translates to a fourth position, wherein said fourth position is greater than said third position.

12. The interbody distractor of claim 11, wherein said first angle, said second angle, said third angle, and said fourth angle are separated by a 90 degree interval.

13. An interbody distractor comprising:
    a height handle comprising a hole;
    an expansion head coupled to said height handle, wherein said expansion head is adapted to be positioned in a vertebral body, wherein said expansion head comprises:
       a first clocking pin;
       a top surface plate and a bottom surface plate positioned opposite to each other;
       a top lifter adapted to lift said top surface plate;
       a bottom lifter adapted to lift said bottom surface plate;
       a head frame body comprising a top extension and a bottom extension, wherein said head frame body is adapted to accommodate said top lifter, and said bottom lifter;
       a first pair of hinge pins adapted to hold said top lifter and said top surface plate such that said top lifter and said top surface plate are held assembled with said head frame body;
       a second pair of hinge pins adapted to hold said bottom lifter and said second surface plate; and a pair of assembly screws adapted to capture said bottom lifter and said bottom surface plate such that said bottom lifter and said bottom surface plate are held assembled with said head frame body, wherein a thickness of said expansion head defines a height of said expansion head, and wherein said expansion head is adapted to be expanded by displacement of said first surface plate and said second surface plate relative to said head frame body causing a height of said expansion head to increase to one of a plurality of heights and causing said first surface plate and said second surface plate to create an angle relative to said head frame body;

a wedge sleeve coupled to said expansion head, wherein said wedge sleeve controls an angle of said top surface plate and said bottom surface plate relative to said head frame body when said wedge sleeve interacts with said top surface plate and said bottom surface plate, wherein said wedge sleeve comprises a first pair of arms, and a second pair of arms, wherein said first pair of arms comprises a first slot, wherein said second pair of arms comprises a second slot, and wherein said first slot and said second slot are adapted to accommodate said head frame body; and a wedge sleeve knob positioned between said height handle and said wedge sleeve, wherein said wedge sleeve knob is adapted to drive said wedge sleeve linearly towards said vertebral body when said wedge sleeve knob is actuated, and wherein a height of said expansion head and an angle of said top surface plate and said bottom surface plate relative to said head frame body are measured by a gauge sleeve coupled to said height handle to determine a height and an angle for an associated implant when said height handle and said wedge sleeve knob are actuated.

14. The interbody distractor of claim 13, wherein said wedge sleeve knob comprises:
a second clocking pin;
a pair of arms adapted to advance said wedge sleeve linearly towards said vertebral body;
said gauge sleeve comprising a first end and a second end, wherein said first end is coupled to said wedge sleeve, wherein said second end is positioned around said height handle, and wherein said gauge sleeve is adapted to translate linearly towards said vertebral body when said pair of arms are actuated;
a wedge sleeve knob housing adapted to accommodate said pair of arms, said first end of said gauge sleeve, and said wedge sleeve; and
a pair of cross pins adapted to assemble said gauge sleeve and said wedge sleeve in said wedge sleeve knob housing.

15. The interbody distractor of claim 13, further comprising:
a second handle coupled to said wedge sleeve;
a middle main shaft adapted to accommodate inside said wedge sleeve;
an inner cam shaft adapted to accommodate inside said middle main shaft, wherein said inner cam shaft comprises a first end and a second end; and
a cam head assembled coaxial with said inner cam shaft, wherein said cam head comprises a first end and a second end, wherein said first end of said cam head is adapted to engage said second end of said inner cam shaft, and wherein said second end of said cam head is adapted to engage said expansion head such that said inner cam shaft enables said second end of said cam head to drive said top lifter and said bottom lifter to lift said top surface angle plate, and said bottom surface angle plate respectively.

16. The interbody distractor of claim 15, further comprising:
a cam shaft fitting comprising a first end and a second end, wherein said first end is adapted to fit in said hole of said height handle, wherein said cam shaft fitting comprises a cross pin hole, wherein said second end is adapted to accommodate said second end of said inner cam shaft; and
a cross pin adapted to be fitted in said cross pin hole such that said cam shaft fitting holds said second end of said inner shaft firmly.

17. A method of operating an interbody device to measure a height and an angle for an associated implant, said interbody device comprising a height handle, a wedge sleeve knob coupled to said height handle, a wedge sleeve coupled to said wedge sleeve knob, a gauge sleeve coupled to said height handle, and an expansion head coupled to said wedge sleeve, wherein said expansion head comprises a top surface angle plate and a bottom surface angle plate, wherein a thickness of said expansion head defines a height of said expansion head, and wherein said expansion head is adapted to be expanded by displacement of said first surface plate relative to said second surface plate causing a height of said expansion head to increase to one of a plurality of heights and causing said first surface plate to create an angle relative to said second surface plate; said method comprising:
positioning said expansion head into a vertebral body;
actuating said wedge sleeve knob such that said wedge sleeve moves linearly towards said vertebral body;
lifting said expansion head; and
measuring, by a gauge sleeve, said height of said expansion head and said angle of said top surface angle plate relative to said bottom surface angle plate of said expansion head when said height handle and said wedge sleeve knob are actuated.

18. The method of claim 17, further comprising positioning a calibrated gauge marker at each position of said height handle and a corresponding height, wherein said expansion head further comprises:
a head frame body coupled to said top surface angle plate and said bottom surface angle plate;
a top lifter positioned between said top surface angle plate and said head frame body; and
a bottom lifter positioned between said bottom surface angle plate and said head frame body.

19. The method of claim 17, further comprising:
adjusting said expansion head to a first height when (i) said height handle is at a first angle, and (ii) said wedge sleeve knob translates to a first position; and
adjusting said expansion head to a second height when (i) said height handle is at a second angle, and (ii) said wedge sleeve knob translates to a second position, wherein said second position is greater than said first position.

20. The method of claim 19, further comprising:
adjusting said expansion head to a third height when (i) said height handle is at a third angle, and (ii) said wedge sleeve knob translates to a third position, wherein said third position is greater than said second position; and
adjusting said expansion head to a fourth height when (i) said height handle is at a fourth angle, and (ii) said wedge sleeve knob translates to a fourth position, wherein said fourth position is greater than said third position.

21. The method of claim 20, wherein said first angle, said second angle, said third angle, and said fourth angle are separated by a 90 degree interval.

22. The method of claim 20, wherein said expansion head is adjusted to at least one of said first height, said second height, said third height, or said fourth height to enable at least one of (i) a distraction of disc space and associated ligamentous tissues, (ii) a correction of spinal deformity, and (iii) an easier insertion of said associated implant in said vertebral body.

* * * * *